United States Patent [19]
Gouterman et al.

[11] Patent Number: 5,965,642
[45] Date of Patent: Oct. 12, 1999

[54] ACRYLIC AND FLUOROACRYLIC POLYMERS FOR OXYGEN PRESSURE SENSING AND PRESSURE-SENSITIVE PAINTS UTILIZING THESE POLYMERS

[75] Inventors: Martin P. Gouterman, Seattle, Wash.; W. Brenden Carlson, Fargo, N. Dak.

[73] Assignee: University of Washington, Seattle, Wash.

[21] Appl. No.: 08/815,144

[22] Filed: Mar. 11, 1997

[51] Int. Cl.$^6$ .................................................. C08K 5/34
[52] U.S. Cl. .................................. 524/88; 524/89
[58] Field of Search ............................ 524/874, 88, 89

[56] References Cited

U.S. PATENT DOCUMENTS

| | | | |
|---|---|---|---|
| 4,752,115 | 6/1988 | Murray | 350/96.29 |
| 4,789,965 | 12/1988 | Michl | 365/121 |
| 4,810,655 | 3/1989 | Khalil | 436/138 |
| 5,043,286 | 8/1991 | Khalil | 436/136 |
| 5,119,463 | 6/1992 | Vurek | 385/129 |
| 5,131,916 | 7/1992 | Eichenauer | 524/88 |
| 5,176,882 | 1/1993 | Gray | 422/82.07 |
| 5,186,046 | 2/1993 | Gouterman | 73/147 |
| 5,271,872 | 12/1993 | Sallavanti | 252/582 |
| 5,307,675 | 5/1994 | Mosharov | 73/147 |
| 5,313,315 | 5/1994 | Feinberg | 359/4 |
| 5,341,676 | 8/1994 | Gouterman | 73/147 |
| 5,631,340 | 5/1997 | Olstein | 528/59 |
| 5,656,241 | 8/1997 | Jeifert | 422/82.06 |
| 5,681,532 | 10/1997 | Kane | 422/82.06 |
| 5,710,197 | 1/1998 | Fischer | 524/83 |

OTHER PUBLICATIONS

J. Kavandi et al., *Rev. Sci. Instum.*, vol. 61, pp. 3340–3347 "Luminescent Barometry in Wind Tunnels" (Nov. 1990).

R. H. Uibel et al., AIAA Paper No. 93–0179, pp. 1–8, "Vide Luminescent Barometry: The Induction Period" (Jan. 1993).

J. P. Bullock et al., Seventh Int'L Symposium, pp. 795–799 "Non–Equilibrium Errors in Pressure Sensitive Paint Measurements" (Sep. 1995).

A.E. Baron et al., *Rev. Sci. Instrum.*, vol. 64 pages 3394–3402 "Submillisecond Response . . . Luminescent Coatings" (Dec. 1993).

*Primary Examiner*—Paul R. Michl
*Attorney, Agent, or Firm*—Lappin & Kusmer LLP

[57] ABSTRACT

The preparation and use of acrylic and fluoroacrylic polymers suitable for luminescence oxygen sensing applications are described. These materials can be used in luminophor coatings for optical fiber sensors or as coatings on aerodynamic surfaces for wind tunnel study. Compositions containing these polymers have the advantages of: (1) reduced induction effect; (2) subsecond response times; (3) low photodegradation; and (4) low temperature dependence.

24 Claims, 8 Drawing Sheets

ACRYLIC AND FLUOROACRYLIC POLYMERS FOR OXYGEN PRESSURE SENSING AND PRESSURE-SENSITIVE PAINTS UTILIZING THESE POLYMERS

The present invention relates generally to acrylic and fluoroacrylic polymers, to pressure-sensitive paint formulations incorporating these polymers, and to an improved method for oxygen pressure sensing using such compositions.

BACKGROUND OF THE INVENTION

This invention relates to oxygen pressure measurements based on the quenching of luminescence of a luminophor or pressure-sensing dye dissolved or dispersed in a polymer matrix which is placed in contact with oxygen-containing gas or liquid. More specifically, pressure sensitive compositions consist of an oxygen permeable polymer matrix into which a fluorescent or phosphorescent dye is either dispersed or dissolved. The luminescence of the dyes that are used in these formulations are quenched in the presence of molecular oxygen. Thus, an increase of molecular oxygen in the polymer matrix results in a decrease of luminescence intensity. The concentration of oxygen in the polymer matrix is dependent on the oxygen pressure or concentration at the surface of the paint. More detailed explanations of the principle of pressure sensitive paint have been previously presented in the literature. In general the polymers are utilized either at the end of an optical fiber or else in a film coating an aerodynamic surface. In the latter case, when the aerodynamic surface is in a wind tunnel and is illuminated by exciting light with the light emission being recorded by a video or CCD camera, the quenching of luminescence can be used to map the pressure differences across the surface due to airflow. In the aerodynamic context, the luminescent coating quenched by oxygen has been referred to in the art as "pressure sensitive paint" or PSP. As in the dictionary definition of "paint," PSP is used herein to refer both to the luminescent coating and to the mixture of pigment, luminophor, vehicle, and additives that is applied to the aerodynamic surface to produce the luminescent coating.

The use of oxygen quenching to measure oxygen pressure has been previously described in U.S. Pat. Nos. 4,810,655; 5,186,046; and 5,341,676, which patents are incorporated herein by reference. U.S. Pat. No. 4,810,655 describes the use of oxygen quenching of a luminophor at the end of an optical fiber to measure oxygen in a fluid, either liquid or gas, an application having particular utility in monitoring the human bloodstream. In the related 5,186,046 and 5,341,676 patents, oxygen quenching is used in connection with wind tunnel research. In these patents, the luminophor is present in a polymer film coated onto the airfoil surface. The effect of aerodynamic lift induced by airflow is to lower the effective oxygen pressure at the surface resulting in less oxygen quenching. The luminescence decay time accordingly lengthens and the luminescence intensity rises. Either of these changes can be monitored and used to measure the pressure changes of interest for aerodynamic studies.

A preferred class of pressure-sensitive dyes for these applications are the porphyrins. Porphyrins are macrocyclic tetrapyrrole structures, some of which are known to luminesce when exposed to specific frequencies of light. This luminescence is also known to be quenched by the presence of oxygen. The oxygen quenching properties of platinum porphyrins have been used for the determination of oxygen in vivo. For aerodynamic pressure studies, the photoluminescence of platinum octaethylporphyrin (PtOEP) is shown to be quantitatively measured as a function of the partial pressure of oxygen with video imaging techniques. When PtOEP in a suitable polymer is applied to an aerodynamic surface and placed in an operating wind tunnel under appropriate lighting, the molecules' luminescence is a function of the local pressure of oxygen over the surface of interest during aerodynamic flow. Since oxygen partial pressure is a fixed fraction of the total air pressure, the resulting image will be brightest in the areas of low pressure and less intense in the areas of high pressure. The luminescence data may later be used to map pressure fields.

Following the initial publication of a description of the use of luminescence paint for pressure measurement in connection with wind tunnel research, many different formulations of polymer with different luminophors have been tried. A familiar and commercially available polymer solvent mix called GP-197, sold by the Genesee Polymers Corporation as a mold release, has been used for PSP with platinum octaethylporphyrin, commonly abbreviated PtOEP, added as the luminophor. The polymer in GP-197 is a silicone resin. Additional details about the GP-197 formulation can be found in J. Kavandi et al., *Rev. Sci Instrum*, vol. 61 at page 3340 (1990). Other relevant prior art publications in this field include B. F. Carroll, et al., *AIAA Journal*, vol. 34 at page 521 (1996); R. H. Uibel, et al., *AIAA Paper* no. 93-0179, 31st Aerospace Sciences Meeting (Jan. 11–14, 1993); and, J. P. Bullock, et al., *Seventh International Symposium on Flow Visualization*, page 795 (Sep. 11–14, 1995).

Testing of PSP based on PtOEP in Genesee-197, however, has led to the discovery of a number of problems and limitations with this PSP formulation. First, it has been found that there exists what might be termed an "induction" effect: the intensity of luminescence increases for a period following the start of illumination thereby leading to inaccuracies in the pressure measuring. Second, the GP-197 formulation was found to respond rather slowly to pressure changes. Response times of tens of seconds were recorded. Because of the expense of wind tunnel research, however, it is desirable to take new wind tunnel readings without having to wait tens of seconds while the luminescence intensity stabilizes. Thus a response time shorter than 1 second is considered highly desirable.

Third, it was found that the luminescence of GP-197 decreased over the time period of irradiation, apparently due to photodegradation of the luminophor. This decrease creates a problem because of the measurement sequence commonly used in wind tunnel studies. Pressure measurement in a wind tunnel is usually determined from the ratio $I_{x,y}$(wind-off,$t_1$)/$I_{xy}$(wind-on,$t_2$), where $I_{xy}$ is the emission intensity recorded on a CCD camera at pixel xy and $t_1$ and $t_2$ are the times when the two measurements are taken. Customarily the $I_{xy}$(wind-off,$t_1$) readings are taken with the wind tunnel off for the series of attack angles of interest. The wind tunnel is turned on and the velocity is adjusted. The $I_{xy}$(wind-on,$t_2$) readings are taken for the same set of attack angles. The wind tunnel velocity can then be adjusted again and another set of $I_{xy}$(wind-on,$t_2$) readings taken. The result is that there can be a considerable period of exposure to exciting light between the times $t_1$ and $t_2$. If there is photodeterioration over this time, a new $I_{xy}$(wind-off) should be taken right before each $I_{xy}$(wind-on) reading. The cost for wind tunnel runs, however, makes it necessary to take only a few $I_{xy}$(wind-off) images. Thus, if $I_{xy}$(wind-off,$t_1$)/$I_{xy}$(wind-on, $t_2$) is to provide an accurate measurement of the pressure on the airfoil, photodegradation between $t_1$ and $t_2$ must be minimized. The PSP based on PtOEP in GP-197 has been found to experience excessive photodegradation over the relevant time period leading to pressure measurement inaccuracies.

A fourth problem with GP-197 in PSP applications is its relatively high temperature dependence. As mentioned above, a considerable time (on the order of tens of minutes) can elapse between I(wind-off,$t_1$) and I(wind-on,$t_2$). Over the course of a wind tunnel run, the temperature in the wind tunnel drifts. Thus, the $I_{xy}$(wind-off,$t_1$) is often taken at a different temperature than $I_{xy}$(wind-on,$t_2$). The GP-197 formulation has been found to have a temperature dependence of nearly 3%/°C. at 1 atm pressure. The temperature in the wind tunnel can drift as much as 40° C. over the course of an all-day wind tunnel run. This introduces a source of serious inaccuracy if there are a few degrees difference in temperature between time $t_1$ for the wind-off image and $t_2$ for the wind-on image. In particular, at low wind velocities where pressure changes due to wind flow are only a few percent of atmospheric pressure, the change in $I_{xy}$(wind-on) due to temperature drift can be of the same order of magnitude or even larger than the change in $I_{xy}$(wind-on) due to pressure. Thus, minimizing the temperature dependence of a PSP formulation is another necessary prerequisite for accurate wind tunnel pressure measurement.

In addition, some other problems became apparent with the GP-197 formulation. It was found to be relatively brittle and would start to chip over the course of a wind tunnel run. On the other hand, GP-197 was easy to apply, it formed a smooth coating that was not sticky, and was relatively rugged to handling. It would therefore be desirable to develop a PSP formulation that eliminates or reduces the four problems mentioned above, while largely preserving the good features of GP-197. These and other problems with and limitations of the prior art PSP formulations in oxygen pressure measuring are, at least in part, overcome with the improved PSP compositions of this invention.

OBJECTS OF THE INVENTION

Accordingly, a general object of this invention is to provide improved polymer binders and pressure-sensitive paint compositions containing these binders for use in oxygen pressure measuring for aerodynamic and other applications.

One specific object of this invention is to provide pressure-sensitive paint compositions that experience little or no induction effects during use.

A second specific object of this invention is to provide pressure-sensitive paint compositions that show relatively rapid responses to pressure changes.

A third specific object of this invention is to provide pressure-sensitive paint compositions that experience only minimal photodegradation over the time period of a single pressure-measurement application.

A fourth specific object of this invention is to provide pressure-sensitive paint compositions that show relatively minimal temperature dependence.

Another object of this invention is to provide pressure-sensitive paint compositions which are easy to apply and form smooth, non-tacky coatings that are relatively rugged, chip-resistant, and do not become brittle.

Yet another object of this invention is to provide pressure-sensitive paint compositions utilizing a class of acrylic and fluoroacrylic polymers in place of silicone resin binders.

Still another object of this invention is to provide improved luminophor compositions containing acrylic or fluoroacrylic polymers suitable for use at the end of an optical fiber or for incorporation in a pressure-sensitive paint for wind tunnel applications.

Other objects and advantages of the present invention will in part be obvious and will in part appear hereinafter. The invention accordingly comprises, but is not limited to, the polymers, compositions and methods of preparing and using those polymers and compositions, involving the several steps and the various ingredients, and the relation and order of one or more such steps and ingredients with respect to each of the others, as exemplified by the following description and accompanying drawings. Various modifications of and variations on the polymers, compositions and methods as herein described will be apparent to those skilled in the art, and all such modifications and variations are considered within the scope of the invention.

SUMMARY OF THE INVENTION

In general, this invention comprises improved luminophor compositions containing a class of acrylic or fluoroacrylic polymers in place of the conventional silicone resin binders. Such compositions are suitable for use at the end of an optical fiber or for incorporation in a pressure-sensitive paint composition for wind tunnel applications. The luminophor compositions of this invention based on acrylic and fluoroacrylic polymers have been found to result in improved performance relative to conventional luminophor compositions in one or more of the following respects: reduced induction effects, relatively rapid response time, reduced photodegradation, lower temperature dependence, easy application, and equal or better surface properties following application.

DETAILED DESCRIPTION OF PREFERRED EMBODIMENTS

Figure 1:
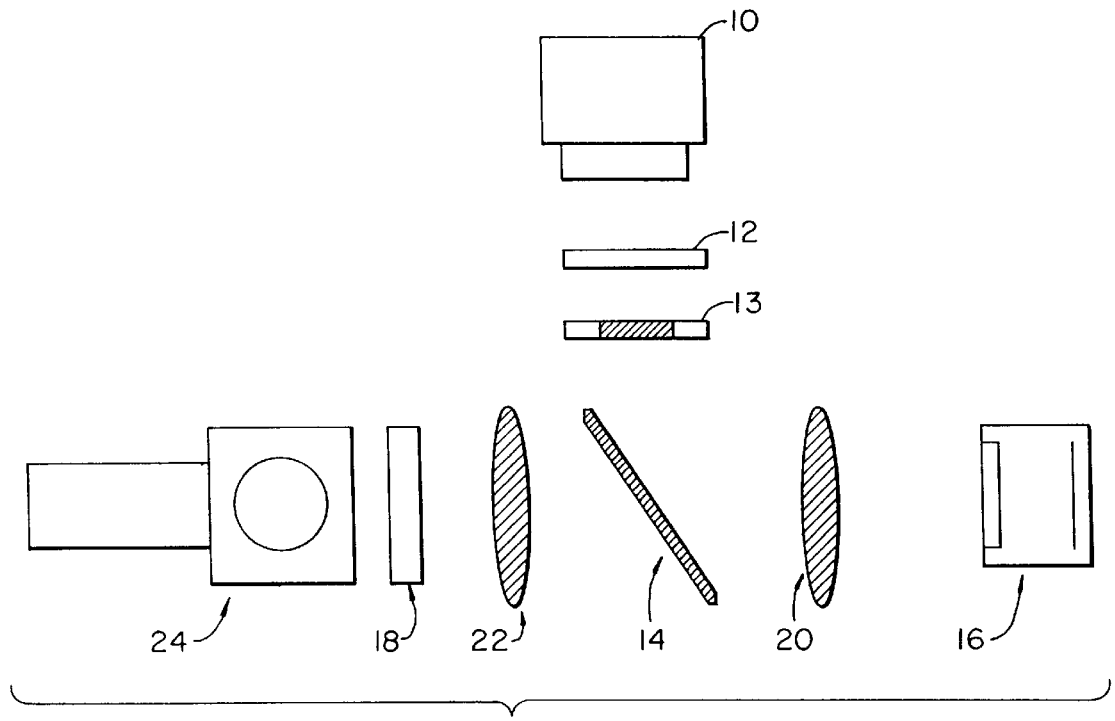
FIG. 1 schematically illustrates certain optical excitation and detection apparatus components which can be used to calibrate the pressure and temperature response of pressure-sensitive paint.

The improved luminophor compositions of the present invention are based on the substitution of particular classes of acrylic, fluoroacrylic, or silyl/siloxy polymers for the silicone resin and similar binders utilized in a conventional luminophor or pressure-sensing dye composition such as GP-197. One class of polymers useful in the practice of this invention comprises acrylic polymers (also called methacrylate polymers) and copolymers having the general configuration illustrated by formula (1) below:

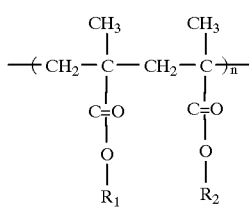

(1)

In formula (1), $R_1$ and $R_2$ are aliphatic or silyl/siloxy side chains, which may be the same or different, and, when different, are randomly distributed along the polymeric backbone. A distribution of n values is expected such that $5n<1000$. The ratio of $R_1$ to $R_2$ side chains in these polymers will vary according to the relative quantities of the starting monomers. For example, the molar ratio of $R_1:R_2$ may range from about 1:10 to 10:1. A preferred acrylic polymer of the formula (1) class is poly (isobutylmethacrylate-co-2-ethylhexyl-methacrylate) (hereinafter "IEMA") wherein $R_1$ comprises an isobutyl group, $R_2$ comprises an ethylhexyl group, and the molar ratio of isobutylmethacrylate monomer to 2-ethylhexylmethacrylate monomer ranges from about 1:4 to 4:1.

In selecting $R_1$ and $R_2$, it has been found that copolymers based on shorter side chains, e.g. methylmethacrylate, show relatively low oxygen permeability, thereby reducing their utility in PSP formulations. When longer aliphatic side chains are substituted for the methyl ester side group, oxygen permeability is increased. On the other hand, the glass transition temperature (Tg) of the copolymer decreases with increased chain length. But substitution of fluorine for hydrogen increases Tg. The chain lengths used here were chosen to maximize oxygen permeability while maintaining a sufficiently high Tg. If Tg is too high compared to the wind tunnel temperatures, the polymer becomes brittle and oxygen permeability is too low for quenching. If Tg is too low, the polymer becomes sticky and it rubs off easily. We estimated the Tg from the Fox equation, which gives 11° C. for IEMA, which is described in Example 1 below, and 70° C. for FIB, which is described in Example 3 below.

EXAMPLE 1

This example illustrates the preparation of an IEMA acrylic copolymer in accordance with the present invention. High-purity liquid monomers, specifically isobutylmethacrylate and 2-ethylhexylmethacrylate monomers, were obtained commercially, such as from Aldrich Chemical Co. The glassware used in this synthesis was thoroughly cleaned before use. 75 mL of isobutylmethacrylate and 100 mL of 2-ethylhexylmethacrylate were mixed together in a 250 mL brown bottle, and 1 gram of activated charcoal was added. The mixture was shaken vigorously. To remove the charcoal, the mixture was then vacuum filtered through a fitted crucible into a filter flask. This process removed the inhibitor from the monomers. The mixture of monomers was then poured from the filter flask into a 500 mL three-necked round bottom flask. A 1.2 times volume amount of toluene was added to the round bottom flask. Then 1/600 molar amount of an initiator AIBN (2,2'-azo-bisisobutyronitrile obtained from Polysciences) was added to the flask. Two rubber septums were placed over two of the necks and a condensing column, attached to a bubbler, was attached to the middle neck. The solution was bubbled vigorously by sending pre-purified nitrogen through a needle in one of the septums. The needle reached to the bottom of the flask. A stir bar also stirred the mixture in the flask. This purging for two hours removed most of the oxygen. The solution was then heated using a water bath to 75° C. and held at that temperature for two days to fully copolymerize the monomers to form IEMA. The toluene solution was then decanted into a 500 mL brown bottle. Small amounts of toluene were used to rinse the round bottom flask, and the liquid was added to the brown bottle until it was filled. The IEMA/toluene solution was then set aside for incorporation into a PSP formulation.

EXAMPLE 2

This example illustrates the preparation of a PSP composition utilizing the IEMA solution of Example 1. 100 mL of the IEMA polymer solution was measured and added to 900 mL of 2-pentanone. To the resulting liter of polymer solution, 100 mg of the luminophor PtTFPP (platinum tetrapentafluorophenylporphyrin) were added and mixed. This composition was now ready to be spray painted onto airfoil surfaces for oxygen pressure measurements.

A second class of acrylic polymers useful in the practice of this invention comprises polyfluorinated or silyl/siloxy homopolymers, copolymers, and terpolymers having the general configuration illustrated by formula (2) below:

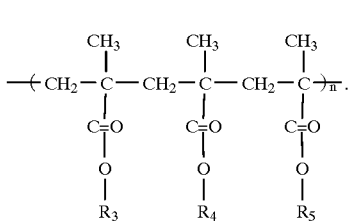

(2)

In formula (2), $R_3$, R4, and $R_5$ are polyfluorinated alkyl side chains or silyl/siloxy side chains, which may be the same or different, and which are randomly distributed along the polymeric backbone. A distribution of n values is expected such that $5<n<1000$. The ratio of $R_3$ to $R_4$ to $R_5$ side chains in the copolymers and terpolymers will vary according to the relative quantities of the starting monomers. For example, the molar ratio of $R_3:R_4$ may range from about 1:10 to 10:1, while the molar ratio of $R_5:(R_3+R_4)$ simultaneously may range from 0:10. Some examples of fluoroacrylic polymers of the formula (2) class useful in this invention include:

poly(2,2,3,4,4,4-hexafluorobutylmethacrylate);

poly(2,2,3,4,4,4-hexafluorobutylmethacrylate-co-1,1,1,3,3,3-hexafluoroisopropylmethacrylate);

poly(1H, 1H,7H-dodecafluoroheptylmethacrylate-co-2,2,3,4,4,4-hexafluorobutylmethacrylate); and poly(1H, 1H,7H-dodecafluoroheptylmethacrylate-co-2,2,3,4,4,4hexafluorobutylmethacrylate-co-1,1,1,3,3,3-hexafluoroisopropylmethacrylate.

It has been found in accordance with this invention that the fluoroalkylmethacrylate polymers of the formula (2) class demonstrate surprisingly superior performance in certain respects relative both to the conventional GP-197 formulations and to the acrylic polymers of the formula (1) class when utilized in oxygen pressure sensing applications. Similar to the acrylic polymers of formula (1), the fluoroalkylmethacrylate polymers of formula (2) provide the advantages of reduced photodegradation, faster response time, and reduced induction effects, in some cases surprisingly superior performance according to these measures. The fluroalkylmethacrylate polymers of formula (2), however, also show a dramatically reduced temperature sensitivity relative to both GP-197 formulations and to compositions containing the acrylic polymers of formula (1).

A useful variant of the methacrylate polymers of formula (1) above and the acrylic polymers of formula (2) above are the silicone methacrylate polymers wherein one or more of the side chains $R_1$ and $R_2$ in formula (1) or $R_3$, $R_4$, and $R_5$ in formula (2) are substituted with a silyl/siloxy side chain. In particular we have used tris(trimethylsiloxy) silylpropylmethacrylate having the formula:

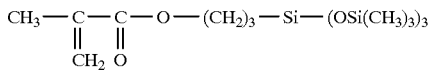

Some examples of such silyl/siloxy acrylic and fluoroacrylic polymers useful in this invention are:

poly(tris(trimethylsiloxy)silylpropylmethacrylate);

poly(isobutylmethacrylate-co-2-ethylhexylmethacrylate-co-tris(trimethylsiloxy)silylpropylmethacrylate);

poly(1,1,1,3,3,3-hexafluoroisopropylmethacrylate-co-2,2,3,4,4,4hexafluorobutylmethacrylate-co-tris(trimethylsiloxy)silylpropylmethacrylate);

poly(1H,1H-dihydroheptafluorobutylmethacrylate-co-tris(trimethylsiloxy)silylpropylmethacrylate); and poly(1,1,1,3,3,3-hexafluoroisopropylmethacrylate-co-1H,1H-dihydroheptafluorobutylmethacrylate-co-tris(trimethylsiloxy)silylpropylmethacrylate).

The first two co-polymers mentioned above are too soft for general wind tunnel work. However, the latter three silyl/siloxy-fluoro acrylic polymers, when compared to GP-197, showed reduced photogredation, faster response time, and reduced induction effects. For the last of these polymers, the temperature dependence was 1.1%C, a factor of 3 lower than with GP-197. With PtTFPP as the luminophor, this silyl/siloxy subclass of fluoroacrylic polymers produced superior pressure sensitive paints as compared with polyfluorinated fluoroacrylic polymers, as described above, but this sublcass of polymers was still not quite as good as the perfluoroacrylic polymers described below.

A further subclass of fluoroacrylic polymers useful in the practice of this invention comprises per-fluorinated alkylmethacrylate homopolymers, copolymers, and terpolymers having the general configuration illustrated by formula (2) above. Because fluorine cannot be located on the same carbon atom as the hydroxyl group of the alcohol, a perfluorinated alcohol is defined as an alcohol with fluorine saturation after the carbon atom. Some preferred perfluoroacrylic polymers useful in the invention include:

poly(1H,1H-dihydroheptafluorobutylmethacrylate);

poly(1H,1H-dihydroheptafluorobutylmethacrylate-co-1H,1H-dihydrotrifluoroethylmethacrylate);

poly(1H,1H-dihydroheptafluorobutylmethacrylate-co-1H, 1H-dihydropentafluropropylmethacrylate);

poly(1H,1H-dihydroheptafluorobutylmethacrylate-co-1,1,1,3,3,3-hexafluoroisopropylmethacrylate), (hereinafter abbreviated as "FIB"); and poly(1H,1H-dihydropentadecafluoro-n-octylmethacrylate-co-1H,1H-dihydroheptafluorobutylmethacrylate-co-1,1,1,3,3,3-hexafluoroisopropylmethacrylate).

It has been found that the subclass of fluoroacrylic polymers in which all the side chains are per-fluorinated (i.e., wherein each of $R_3$, $R_4$ and $R_5$ in formula (2) represents a perfluorinated alcohol group) demonstrates surprisingly superior performance in certain respects relative to the conventional GP-197 formulations and also compared to the acrylic polymers of formula (1) and the earlier-described polyfluorinated fluoroacrylic polymers of formula (2). With respect to at least one common luminophor, PtTFPP, the use of per-fluorinated acrylic polymers of the formula (2) class has been found to significantly reduce photodegradation of this pressure-sensing dye, even as compared with the polyfluorinated fluoroacrylic polymers of formula (2). With respect to response time, PSP formulations based on the per-fluorinated acrylic polymers of the formula (2) class have been found to respond about equally as rapidly as the polyfluorinated fluoroacrylic polymers of formula (2). Similarly, with respect to reduction of the undesired induction effect, all fluoroacrylic polymers of formula (2) have been found about equally successful.

With respect to temperature dependence, however, again significant improvement in results has been found with the per-fluorinated acrylic polymers of formula (2). It was found that PSP formulations utilizing polyfluorinated fluoroacrylic polymers of the formula (2) type reduced temperature dependence by a factor of two relative to the GP-197 standard. By contrast, PSP formulations based on the perfluorinated acrylic polymers of formula (2) have shown a reduced temperature dependence by a factor of five compared with GP-197.

EXAMPLE 3

This example illustrates the preparation of a perfluorinated acrylic polymer of the formula (2) class, specifically a fluoro-isopropyl-butyl (FIB) copolymer based on the liquid monomers 1,1,1,3,3,3-hexafluoroisopropylmethacrylate and 1H,1H-dihydroheptafluorobutylmethacrylate, purchased from PCR Chemicals, Inc. These monomers come packed in 100 g samples in brown bottles. To each 100 g sample was added 0.5 g of activated charcoal. The bottles were then shaken vigorously by hand for a few seconds. After letting them sit for 5 minutes, each monomer/activated charcoal mixture was filtered as described in Example 1 above. The monomers were then poured into a three-necked 500 mL round bottom flask and 215 mL of α,α,α-trifluorotoluene was added. To this flask, 1/800 molar amount of an initiator, laurel peroxide, was added. Nitrogen was bubbled through this liquid for two hours using the technique described for Example 1. A stir bar was also used. The solution was then heated using a water bath to 64° C. and held at that temperature for two days. The solution was then heated to 100° C. and held at that temperature for an additional eight hours to fully copolymerize the monomers to form FIB. The trifluorotoluene solution was then decanted into a 500 mL brown bottle and small amount of trifluorotoluene was used to rinse the round bottom flask, and the liquid was added to the brown bottle until it was filled. The FIB/trifluorotoluene solution was then set aside for incorporation into a PSP formulation.

EXAMPLE 4

This example illustrates the preparation of a PSP composition utilizing the FIB solution of Example 3. 90 mL of the FIB polymer solution was measured and added to 900 mL of a 50:50 volume mixture of 2-pentanone and butylacetate. To this solution was added 100 mg of the luminophor PtTFPP. Additives (e.g. 4 g of hydrated $Al_2O_3$) can also be introduced at this point. This requires ball milling. The paint as formulated is now ready to be sprayed onto a white basecoat, as described below.

It has further been found in accordance with this invention that the PSP formulations described above perform well when coated on a white undercoat, as discussed with respect to conventional PSP compositions in the aforementioned U.S. Pat. Nos. 5,186,046 and 5,341,676. The effect of a white undercoat is to increase the observed luminescence light intensity. At the same time, use of such an undercoat may also result in certain disadvantages or undesirable effects such as increasing the response time to pressure change if the undercoat dissolves oxygen. We have found that FIB can be used to form a particularly good white base coat useful for the polymer paints and for other pressure sensitive paints. It shows none of the adverse side effects shown by other commercial white paints.

The advantages of PSP formulations utilizing the novel polymers of this invention will be better understood by reference to the several drawings and figures as described below.

FIG. 1 schematically illustrates the various optical components used in the laboratory work to gather comparative data on the respective luminescence responses to oxygen of conventional PSP formulations and PSP formulations utilizing the novel acrylic and fluoroacrylic polymers of this invention. Light from the quartz tungsten halogen lamp 10 passes through the excitation filter 12 and shutter 13. Filter 12 transmits light in a range (usually 350 to 450 nm) suitable for exciting Pt porphyrin to the luminescing triplet excited state. The dichroic mirror 14 transmits longer wavelength light while short wavelength light in the range of 450 to 350 nm is reflected into the cell 16 that contains the PSP sample to be tested. The emitted light centered at 640 nm exits from the cell 16, passes through two focusing lenses 20,22, the dichroic mirror 14, and the emission filter 18 before impinging on the photomultiplier tube (PMT) detector 24. The excitation and emission filters, 12 and 18 respectively, are chosen so that no light from the exciting lamp 10 passes through to the detector 24.

Figure 2:
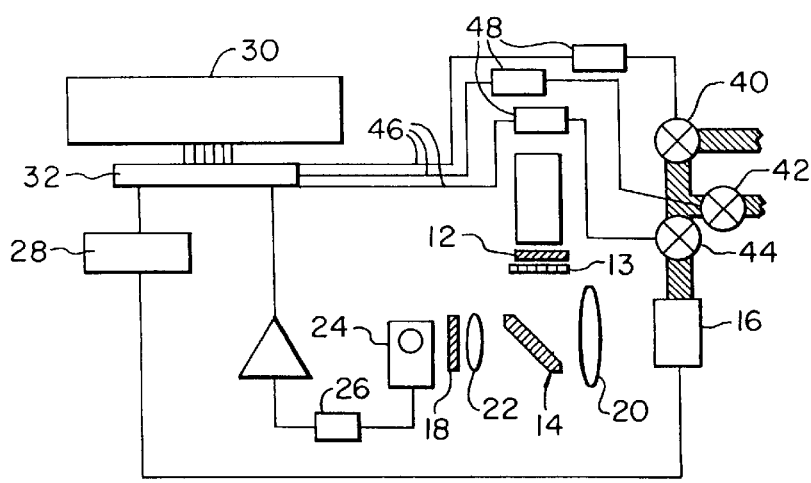
FIG. 2 schematically illustrates one type of computer control and gas handling system that allows luminescence intensity data to be monitored as a function of time, temperature, and pressure as desired.

FIG. 2 shows the optical excitation and detection apparatus of FIG. 1 embedded in the larger computer controlled apparatus that allows pressure and temperature control and light measurement. The excitation and emission filters 12 and 18, lenses 20 and 22, the dichroic mirror 14, and the Uniblitz shutter 13 are all as shown in FIG. 1. In addition FIG. 2 shows the sample cell holder 16 with asssociated pressure and temperature control 28, the PMT 24, and the pre-amplifier 26 connected to the computer 30 through the A/D board 32. FIG. 2 also shows the computer control for the gas handling system, which has three valves 40, 42 and 44 that are computer controlled through transistor-transistor logic circuitry 46 associated with solid state switches 48. One valve 42 vents to the air, the second valve 40 opens to a vacuum, and the third valve 44 is a specially designed proportional valve that can be opened a small amount and quickly closed.

To illustrate how this apparatus works, we describe below how a typical Stern-Volmer plot, I(P,T) versus P at fixed T, is taken over the pressure range from 1 atm to 0 atm. The computer control sets the temperature, T, of the sample cell S. The vent valve to the air and the proportional valve are then closed and the vacuum valve is opened. The proportional valve is then opened a small amount and the pressure is continuously monitored. After the desired pressured drop, the proportional valve is closed. Some time is then allowed for the cell to come to pressure and temperature equilibrium and then the pressure, P, and luminescence intensity I, are recorded by the computer. The proportional valve is then opened again and a new pressure obtained. It can be seen that if, say, 10 pressure steps between 1 atm and vacuum are desired, the pressure steps over the run will not be precisely equal. But since the computer records the precise equilibrium pressure and intensity, the data provides accurate Stern-Volmer curves.

In a similar way, other computer programs allow the various types of data to be obtained from this one apparatus. In particular this apparatus may be used to measure the following critical properties of a PSP composition: time response, I(t) after a pressure jump; photodegradation, I(t) over an extended period of illumination; Stern-Volmer plots, I(P,T) at fixed temperature T as P is varied in steps from 1 atm to vacuum or from vacuum to 1 atm; and I(P,T) at fixed pressure P as T is varied over a range between limits 5° C. and 50° C.

Figure 3:
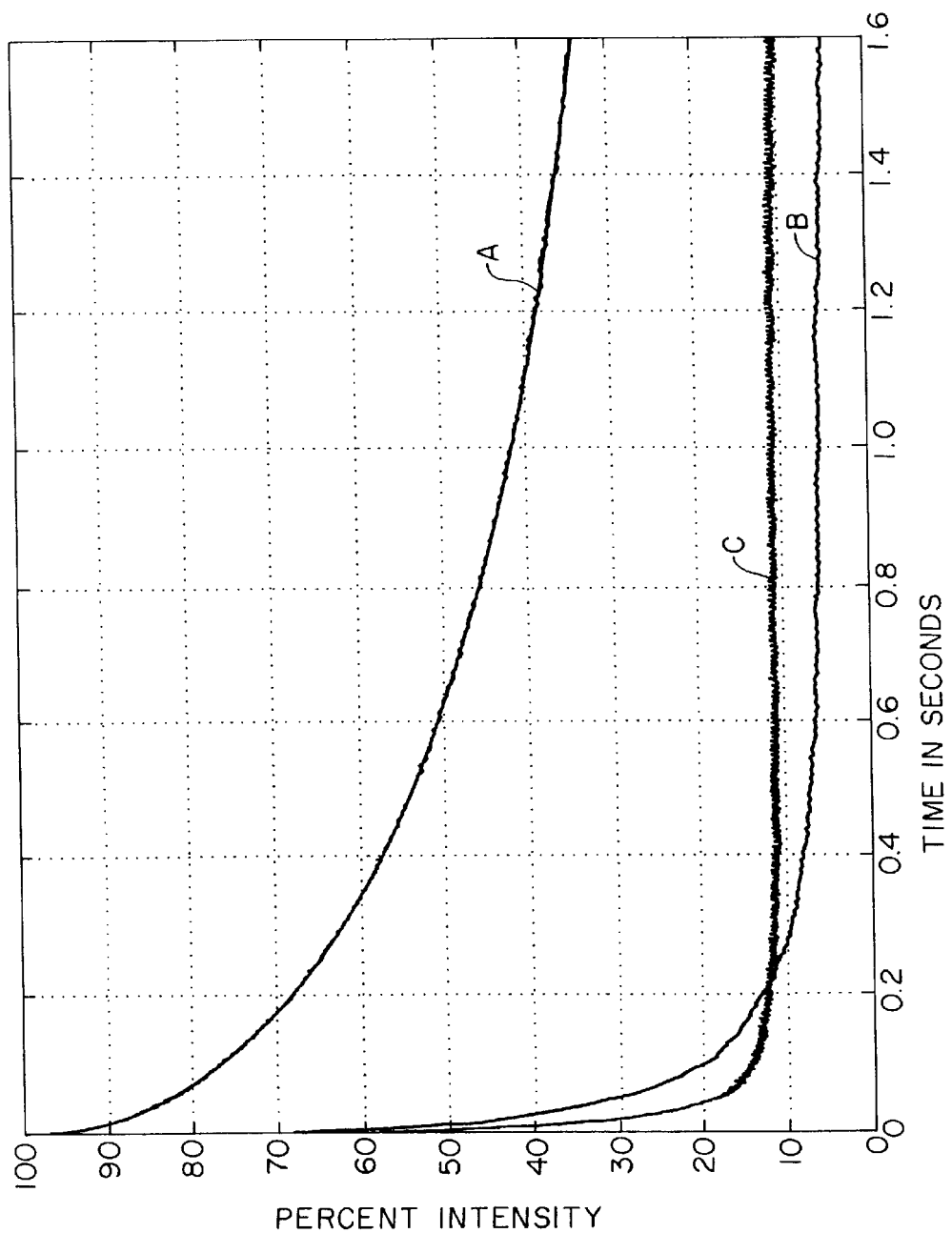
FIG. 3 is a graph comparing the luminescence intensity response over time, following a pressure increase, of a single luminophor in three difference luminophor compositions, one a prior art composition and two in accordance with this invention.

FIG. 3 illustrates the improvement in response time obtained by using PSP formulations based on the novel polymers of this invention by plotting percent luminescence intensity against time in seconds for three compositions following a pressure jump from 0 to 1 atm. While independent measurements of the pressure drop for this apparatus shows the pressure change is complete in about 10 milliseconds, luminescence intensity falls over a much longer period of time, called the "response time," from its high value in vacuum to its much lower equilibrium value at 1 atm. The three curves in FIG. 3 represent the luminescence intensity of PtOEP as a function of time following the pressure jump for three different PSP formulations: Curve A is the standard GP-197, while curve B represents a PSP formulation using the IEMA polymer prepared according to Examples 1 and 2, and curve C represents a PSP formulation based on the FIB polymer prepared according to Examples 3 and 4. It can be seen that, after 1.6 seconds, curve A is still in a region of steep decline and is nowhere near its final intensity. However for both the IEMA formulation, curve B, and the FIB formulation, curve C, the intensity has reached its final value, 6% and 11 %, respectively, by 1 second. Thus, for the IEMA and FIB compositions, within 1 second of changing a wind tunnel parameter, e.g. the angle of attack, the luminescence intensity has reached its final value. This short response time also leads to minimization of any induction effect, which has been a serious problem for the GP-197 polymer composition. Accordingly, the IEMA and FIB polymer formulations of curves B and C respectively show dramatic and wholly unexpected improvement in response time relative to the GP197 composition. It might be noted in FIG. 3 that the FIB formulation responds to the pressure change rather more quickly than IEMA at short times, but both formulations require 1 second to reach their final values.

Figure 4:
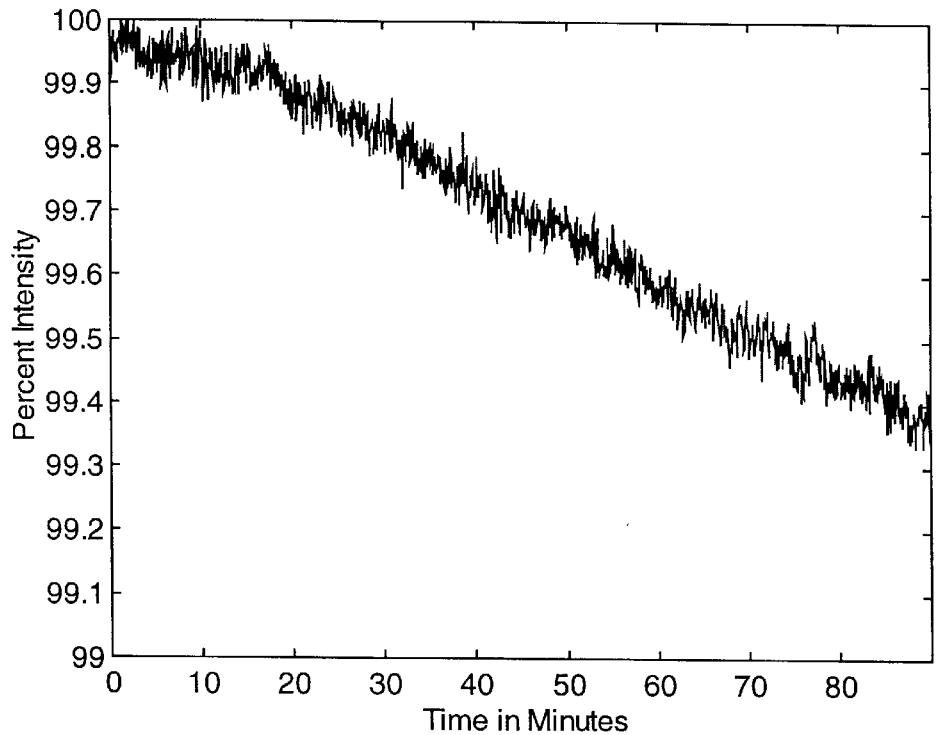
FIG. 4 is a graph showing degradation over time of a first luminophor composition in accordance with this invention.
Figure 5:
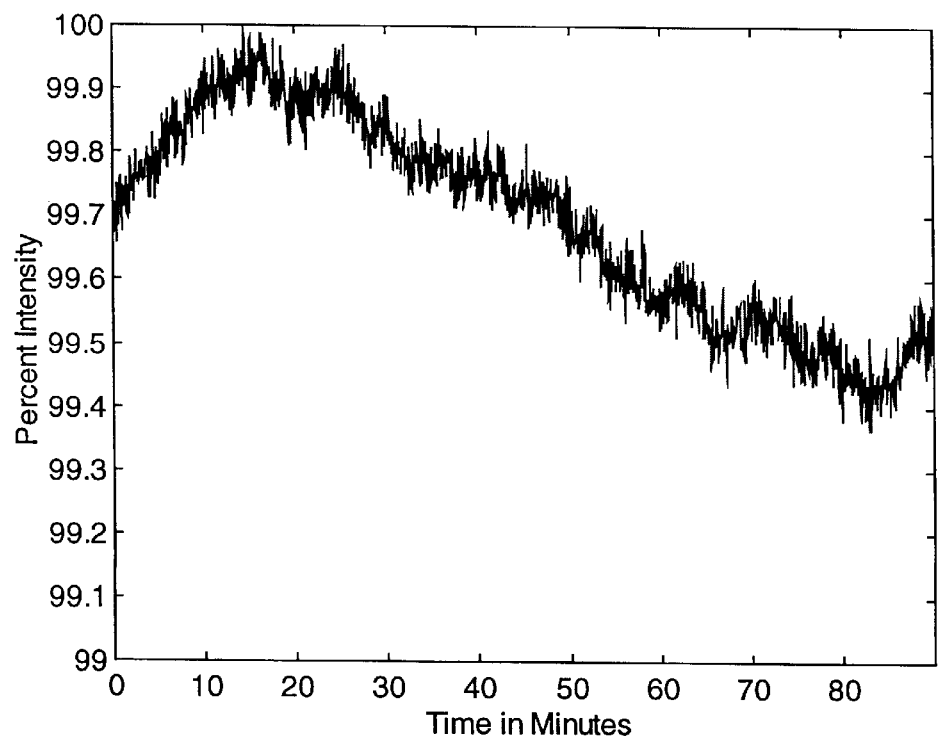
FIG. 5 is a graph showing degradation over time of a second luminophor composition in accordance with this invention.

FIG. 4 illustrates the reduced rate of photodegradation of the luminophor PtTFPP in an IEMA polymer formulation prepared according to Examples 1 and 2. After about one and one-half hours, the luminophor retains about 99.4% of its original luminescence intensity. Similarly, FIG. 5 illustrates the reduced rate of degradation of the luminophor PtTFPP in an FIB polymer formulation prepared according to Examples 3 and 4. Again, after about one and one-half hours, the luminophor retains about 99.5 % of its original luminescence intensity. Indeed the intensity changes in FIGS. 4 and 5 are so small that they may merely represent lamp drift. In sharp contrast, under the same conditions, PtOEP in the GP-197 formulation photodegrades to roughly 30% of its original intensity after one and one-half hours of exposure to the same level of exciting light.

Figure 6A:
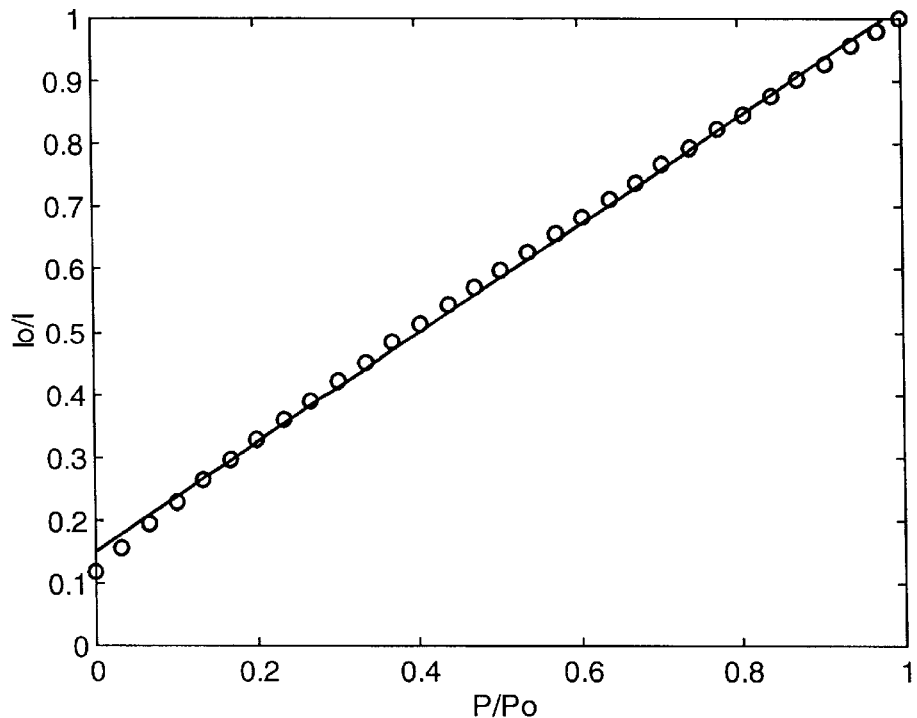
FIGS. 6A and 6B are Stern-Volmer calibration curves at 25° C. fitted to the data points by different techniques for a luminophor in a first luminophor composition in accordance with this invention.
Figure 6B:
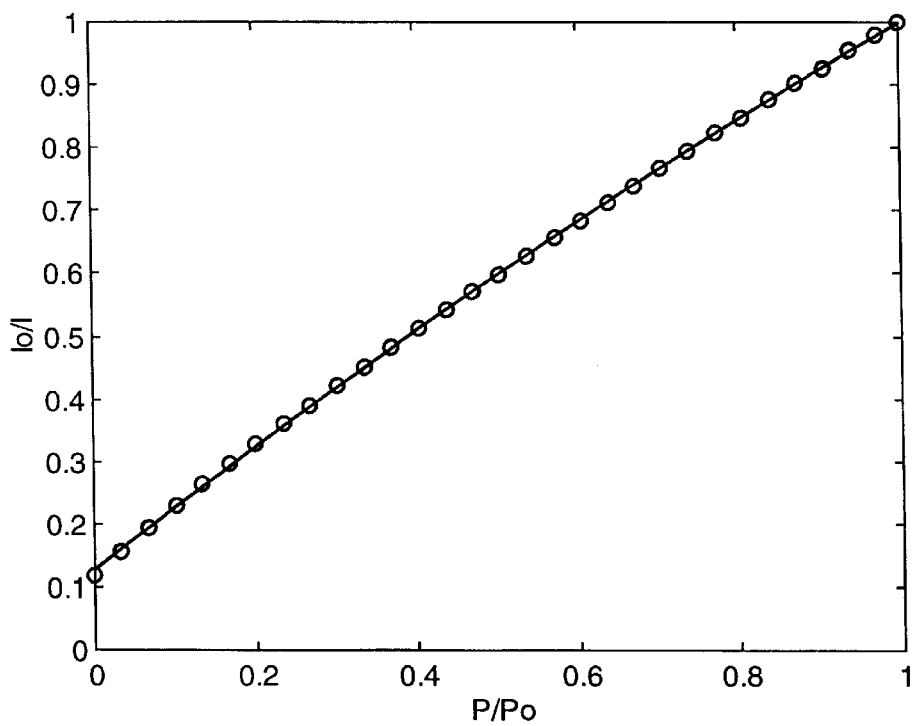

FIGS. 6A and 6B show $I(P_0,T)/I(P,T)$ for PtTFPP in IEMA versus $P/P_0$ at T=25° C. (In the graphs the axis is labeled $I_0/I$.) In FIG. 6A the intensity data is fitted to a linear function of $P/P_0$ and in FIG. 6B to a quadratic function of $P/P_0$. The quadratic fit, which works quite well except at the lowest pressures, is quite satisfactory for wind tunnel applications.

Figure 7A:
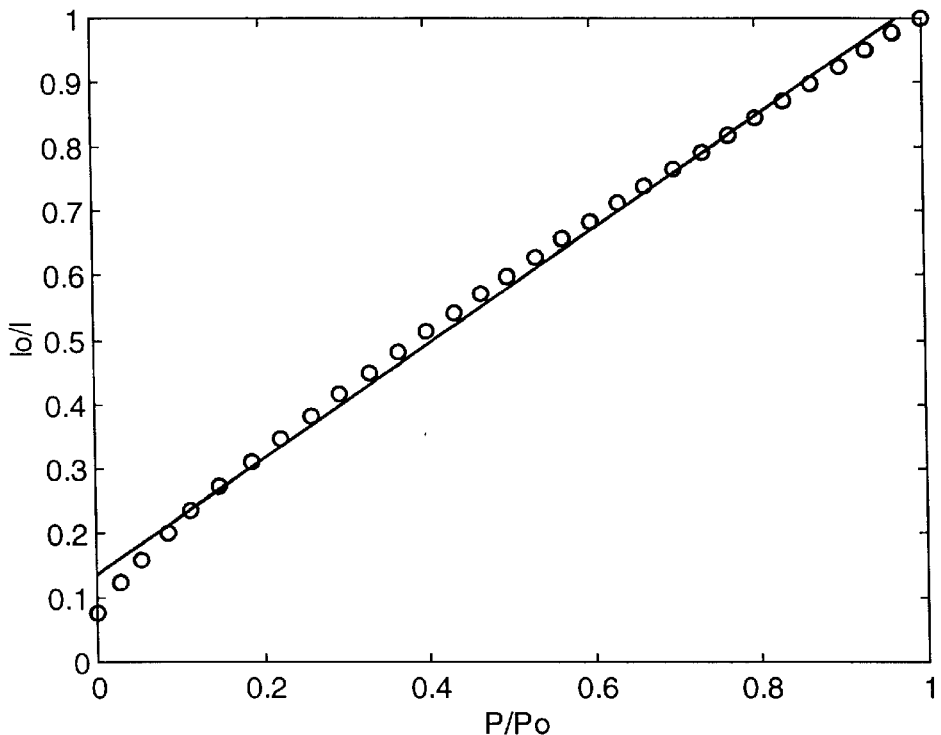
FIGS. 7A and 7B are Stern-Volmer calibration curves at 25° C. fitted to the data points by different techniques for a luminophor in a second luminophor composition in accordance with this invention.
Figure 7B:
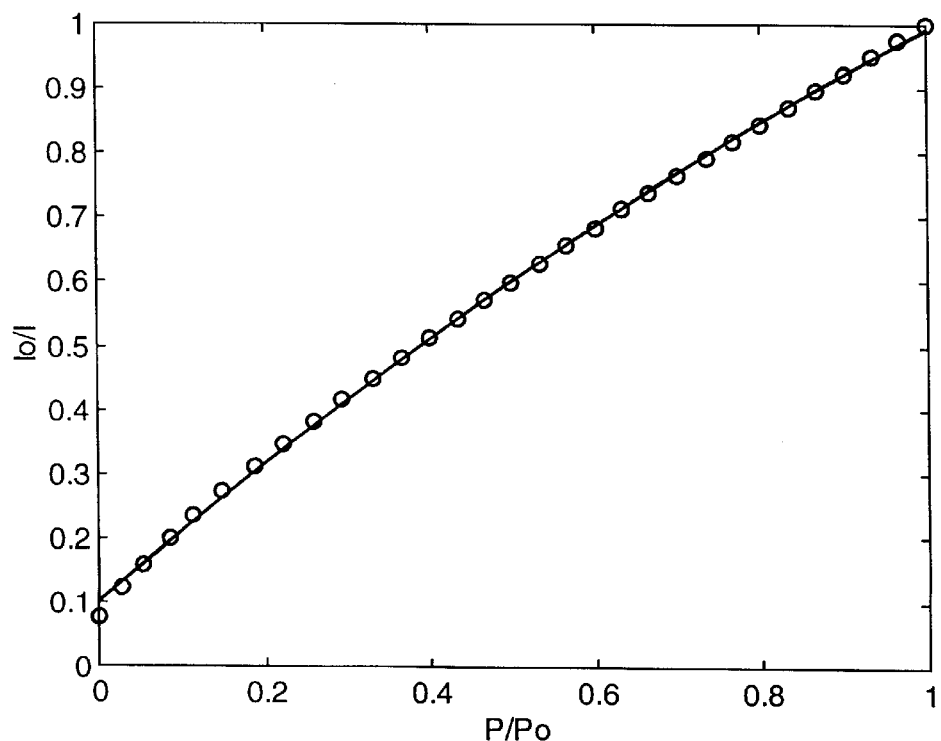

FIGS. 7A and 7B show $I(P_0,T)/I(P,T)$ for PtTFPP in FIB versus $P/P_0$ at T=25° C. The linear fit in FIG. 7A for FIB is slightly poorer than that in FIG. 6A for IEMA, but the quadratic fits works equally well in FIG. 7B as in FIG. 6B and is suitable for wind tunnel applications.

Figure 8A:
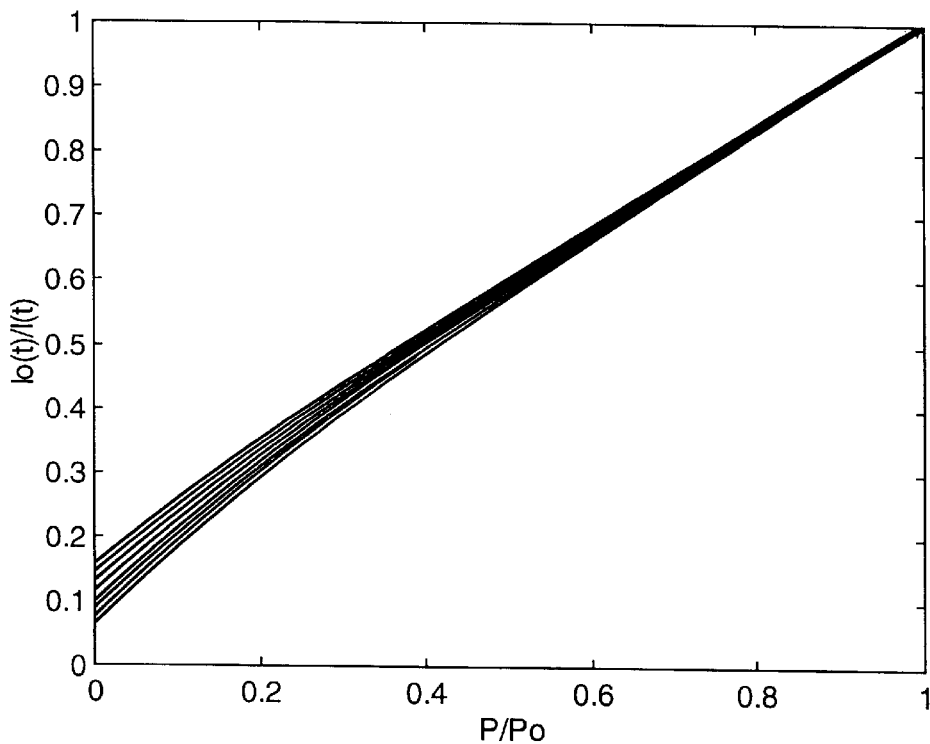
FIGS. 8A and 8B are Stern-Volmer plots at different temperatures for a first luminophor composition in accordance with this invention over a temperature range of 5° C. to 45° C.
Figure 8B:
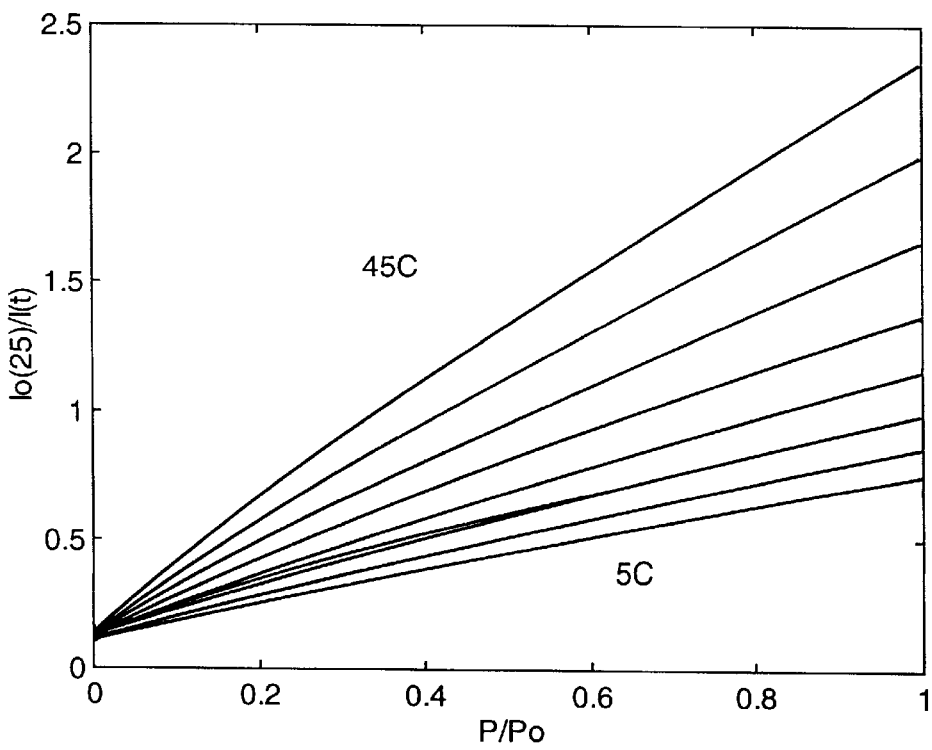

FIGS. 8A and 8B show the temperature sensitivity of the PtTFPP in IEMA formulation, displaying the same data in two ways. FIG. 8A plots $I(P_0,T)/I(P,T)$ versus $P/P_0$. (In the graphs the axis is labeled $I_0(t)/I(t)$.) By definition $I(P_0,T)I(P,T)=1$ when $P/P_0=1$ for all values of T. However the plots of $I(P_0,T)/I(P,T)$ diverge as a function of T for $P/P_0 < 1$. In FIG. 8B the very same data is displayed as $I(P_0,25°$ C.$)/I(P,T)$ versus $P/P_0$. (In the graphs the axis is labeled $I_0(25)/I(t)$.) The considerable temperature dependence of these plots is apparent in FIG. 8B, indicating the high temperature sensitivity of this formulation.

Figure 9A:
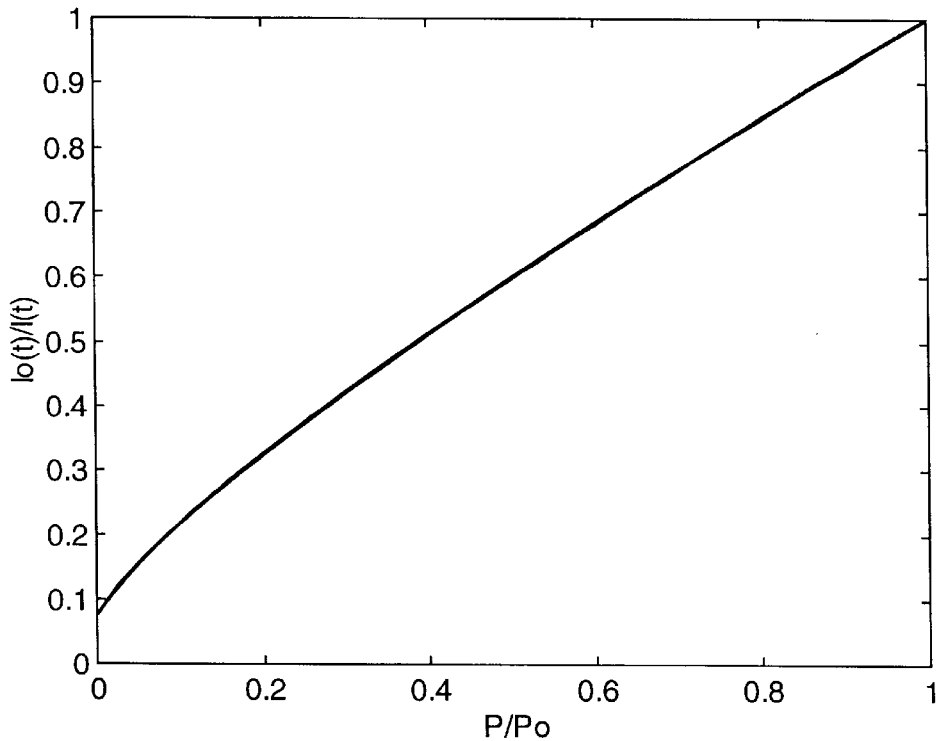
FIGS. 9A and 9B are Stern-Volmer plots at different temperatures for a second luminophor composition in accordance with this invention over a temperature range of 10° C. to 50° C.
Figure 9B:
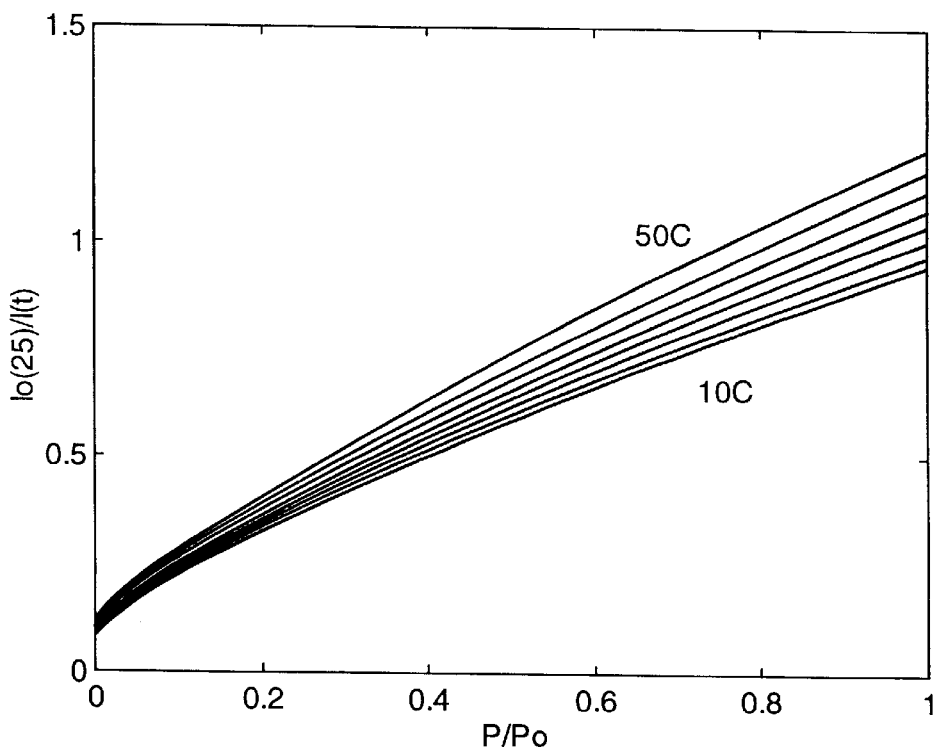

FIGS. 9A and 9B show the same type of intensity ratio plots for the PtTFPP in FIB formulations as FIGS. 8A and 8B show for PtTFPP in IEMA. Note that the curves $I(P_0,T)/I(P,T)$ in FIG. 9A are superposed and do not diverge as a function of T as do the curves in FIG. 8A. Also, comparing $I(P_0,25°$ C.$)/I(P,T)$ in FIG. 8B for PtTFPP in IEMA with the same type of data in FIG. 9B for PtTFPP in FIB, clearly there is much less temperature dependence for the PtTFPP in FIB.

The superposition of the curves in FIG. 9A shows that for PtTFPP in FIB the function $I(P,T)$ can be expressed as a production function according to equation (1) below:

$$I(P,T)=I^a(P)I^b(T) \qquad eq.(1)$$

a condition that does not hold for the curves in FIG. 8A for PtTFPP in IEMA. We call such PSP formulations "ideal pressure paints." In wind tunnel studies the actually intensity ratio is measured as $I_{xy}(P_0,T_0)/I_{xy}(P_{xy},T_{xy})$ where $P_0$ and $T_0$ are the pressure and temperature for the pixels xy of the CCD camera of the wind-off image while $P_{xy}$ and $T_{xy}$ are the pressure and temperature at pixel xy for the wind-on image. (In this discussion, for simplicity we assume there is no model motion between wind-off and wind-on.) For an ideal PSP, the measured ratio is represented by equation (2) below:

$$I_{xy}(P_0,T_0)/I_{xy}(P_{xy},T_{xy})=I^a_{xy}(P_0)I^b(T_0)/I^a_{xy}(P_{xy})I^b(T_{xy}) \qquad eq.(2)$$

Hence a temperature corrected ratio can be obtained as equation (3) below:

$$[I_{xy}(P_0,T_0)/I_{xy}][I^b(T_{xy})/I^b(T_0)]=I^a_{xy}(P_0)/I^a_{xy}(P_{xy}) \qquad eq.(3)$$

Thus, if the temperature for the wind-on image is known, the factor $I^b(T_{xy})/I^b(T_0)$ can be used to correct the image ratio taken with wind-on and wind-off at different temperatures. The function $I^b(T)$ can be determined from laboratory measurements. If the temperature gradients over the wind-on image are small, one factor $[I^b(T)/I^b(T_0)]$, where T is the average wind-on temperature, can correct the entire image ratio. Thus not only does PtTFPP in FIB show less temperature dependence than PtTFPP in IEMA, but also, because it is an ideal PSP, it is potentially easier to correct for a temperature change between the wind-off and wind-on images.

Figure 10:
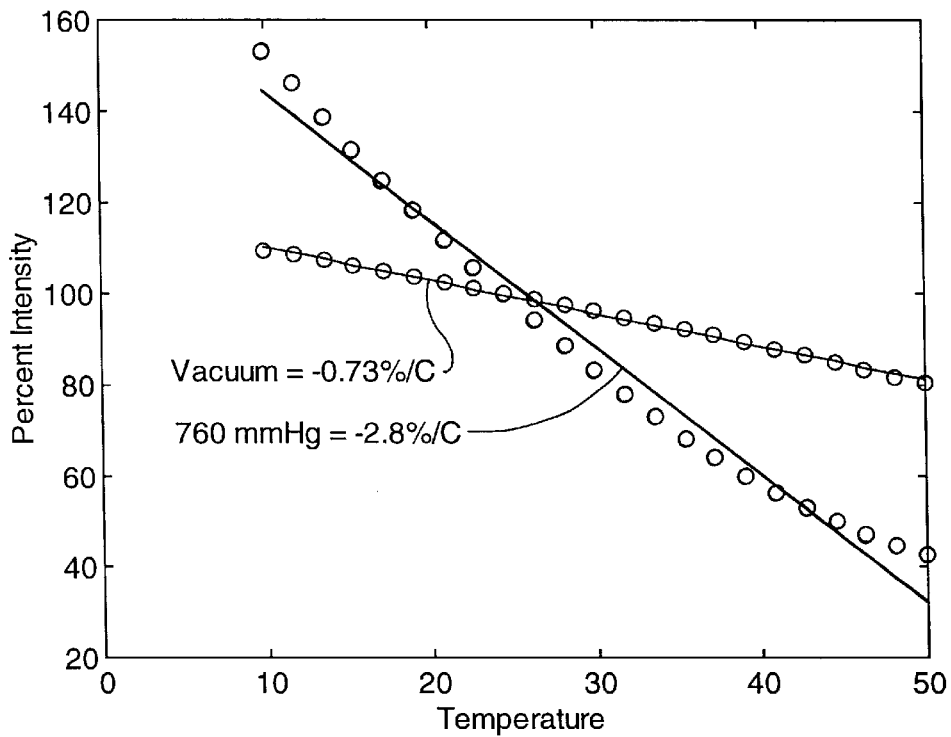
FIG. 10 is a graph showing luminescence intensity as a function of temperature at two pressures for a first luminophor composition in accordance with this invention.
Figure 11:
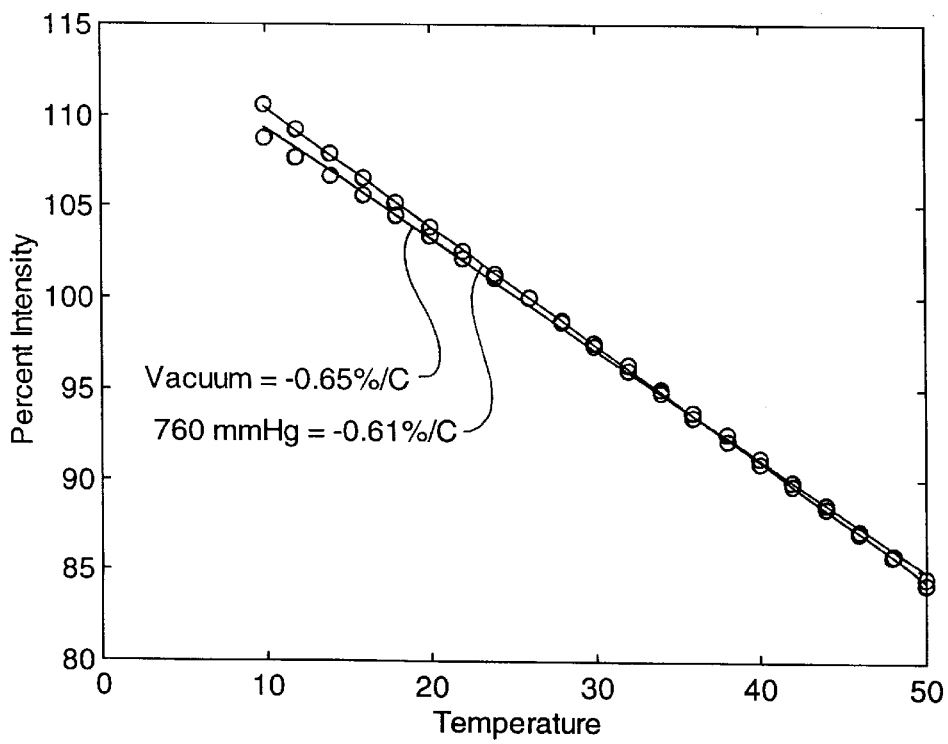
FIG. 11 is a graph showing luminescence intensity as a function of temperature at two pressures for a second luminophor composition in accordance with this invention.

Another way to compare response curves of two different PSP formulations is to plot percent luminescence intensity against temperature at two different pressures. FIGS. 10 and 11 compare the temperature dependence of the luminescence intensity of PtTFPP in, respectively, IEMA and FIB, over the temperature range 10° C. to 50° C. In each graph one curve shows data taken at atmospheric pressure while the second curve plots data taken under vacuum conditions. In all cases percent intensity is seen to decrease with higher temperatures. However IEMA and FIB behave quite differently. The slope for IEMA changes from −0.73%/°C. to −2.8%/°C. between vacuum and one atmosphere. However the slope for FIB is essentially the same, −0.65%/°C. and −0.61%/°C. at vacuum and one atmosphere. The fact that the slope is independent of pressure is another way to see that FIB is an "ideal pressure paint" as described by eq. (1) while IEMA is not. It further illustrates the superiority of the per-fluorinated acrylic polymers of this invention for PSP applications.

The following experimental data further illustrates the advantages and superiority of PSP compositions according to this invention (Samples #3, and 4) relative to several prior art formulations (Samples #1 and 2). Table 1 below qualitatively compares physical and performance characteristics of the four sample PSP compositions when applied to an aerodynamic surface.

TABLE 1

| Sample # | Polymer Type & Source | Advantages | Disadvantages |
|---|---|---|---|
| 1 | highly cross-linked silicone polymer made by Genesee Polymers | Hard, smooth surface. Bright luminescence. | Chips easily, slow response, fast degradation, temperature dependent. |
| 2 | polydimethyl-siloxane and poly-carbonate polymer made by General Electric | Low degradation, fast response, bright luminescence. | Orange peel effect, peels off wing in wind tunnel tests, non homogenous surface, temperature dependent. |
| 3 | IEMA/PtFPP- prepared according to this invention | Low degradation, fast response, wide dynamic range, durable in wind tunnels, inexpensive | still shows serious temperature dependence |
| 4 | FIB/PtFPP- prepared according to this invention | Lower temperature dependence, very wide dynamic range with PtTFPP, hard, durable surface, low degradation | most expensive of the binders |

Table 2 below quantitatively compares certain performance characteristics of the four sample PSP compositions when applied to an aerodynamic surface.

TABLE 2

| Sample # | Dye | Dynamic Range | Temperature Dependence (%/° C.) atm. | Temperature Dependence (%/° C.) vac. | Degradation (% in 90 min) |
|---|---|---|---|---|---|
| 1 | PtTFPP | 70% | −2.90 | −0.65 | −60% |
| 2 | PtTFPP | 60% | −1.60 | −0.65 | −1.5% |
| 3 | PtTFPP | 90% | −3.40 | −0.60 | <0.6% |
| 4 | PtTFPP | 92% | −0.61 | −0.65 | <0.6% |

It will be apparent to those skilled in the art that other changes and modifications may be made in the above-described compounds, compositions, and methods for making and using the same without departing from the scope of the invention herein, and it is intended that all matter contained in the above description shall be interpreted in an illustrative and not in a limiting sense.

Having described the invention, what we claim is:

1. A pressure-sensitive paint composition for coating a surface for oxygen pressure sensing applications, said composition consisting essentially of a polymeric binder and an oxygen pressure sensing dye, wherein said binder is selected from the group consisting of:

A. a fluoroacrylic polymer having the configuration:

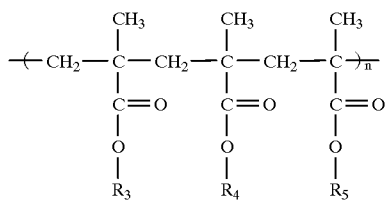

wherein $R_3$, $R_4$ and $R_5$ are selected from the same or different polyfluorinated alkyl side chains, $R_3$, $R_4$ and $R_5$ occur in random order, and n is a distribution of integers such that $5<n<1000$; and, B. a polyfluorinated acrylic polymer having the configuration:

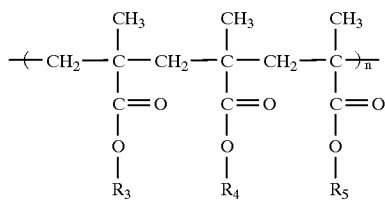

wherein at least one of $R_3$, $R_4$ and $R_5$ is selected from the group consisting of perfluorinated or dihydroperfluorinated alkyl side chain and the remaining two side chains are selected from the same or different perfluorinated or dihydroperfluorinated alkyl side chains or polyfluorinated alkyl side chains, $R_3$, $R_4$ and $R_5$ occur in random order, and n is a distribution of integers such that $5<n<1000$.

2. A pressure-sensitive point composition according to claim 1 wherein said pressure-sensing dye is selected from the group consisting of platinum octaethylporphyrin and platinum tetrapentafluorophenylporphyrin.

3. A pressure-sensitive paint composition according to claim 1 wherein said pressure -sensing dye is selected from the group consisting of platinum octaethylporphyrin and platinum tetapentafluorophenylporphyrin, and said binder is selected from the group consisting of:

poly(2,2,3,4,4,4-hexafluorobutyl methacrylate);

poly(1H,1H-dihydroheptafluorobutylmethacrylate);

poly(1,1,1,3,3,3-hexafluoroisopropyl methacrylate-co-2,2,3,4,4,4-hexafluorobutyl methacrylate);

poly(1,1,1,3,3,3-hexafluoroisopropyl methacrylate-co-2,2,3,4,4,4-hexafluorobutyl methacrylate-co-1H,1H,7H-dodecafluoroheptyl methacrylate);

poly(2,2,3,4,4,4-hexafluorobutyl methacrylate-co-1H,1H,7H-dodecafluoroheptyl methacrylate);

poly(1H,1H-dihydroheptafluorobutylmethacrylate-co-1H,1H-dihydropentafluoropropylmethacrylate);

poly(1H,1H-dihydroheptafluorobutylmethacrylate-co-1H,1H-dihydrotrifluoroethylmethacrylate);

poly(1H,1H-dihydropentafluoropropylmethacrylate-co-1H,1H-dihydrotrifluoroethylmethacrylate);

poly(1H,1H-dihydroheptafluorobutylmethacrylate);

poly(1H,1H-dihydroheptafluorobutylmethacrylate-co-1,1,1,3,3,3-hexafluoroisopropylmethacrylate);

poly(1H,1H-dihydroperfluoro-n-octylmethacrylate-co-1H,1H-dihydroheptafluorobutylmethacrylate-co-1,1,1,3,3,3-hexafluoroisopropylmethacrylate);

poly(1H,1H-dihydropentadecafluoro-n-octylmethacrylate-co-1H,1H-dihydroheptafluorobutylmethacrylate-co-1,1,1,3,3,3-hexafluoroisopropylmethacrylate);

poly(1H,1H-dihydroperfluoro-n-octylmethacrylate-co-1H,1H-dihydroheptafluorobutylmethacrylate-co-1,1,1,3,3,3-hexafluoroisopropylmethacrylate);

poly(1,1,1,3,3,3-hexafluoroisopropylmethacrylate-co-2,2,3,4,4,4-hexafluorobutylmethacrylate-co-tris(trimethylsiloxy)silylpropylmethacrylate);

poly(1H,1H-dihydroheptafluorobutylmethacrylate-co-tris(trimethylsiloxy)silylpropylmethacrylate); and poly(1,1,1,3,3,3-hexafluoroisopropylmethacrylate-co-1H,1H-dihydroheptafluorobutylmethacrylate-co-tris(trimethylsiloxy)silylpropylmethacrylate).

4. A pressure-sensitive paint composition for coating a surface for oxygen pressure sensing applications, said composition consisting essentially of a polymeric binder and an oxygen pressure-sensing dye, wherein said binder consists essentially of a fluoroacrylic polymer having the configuration:

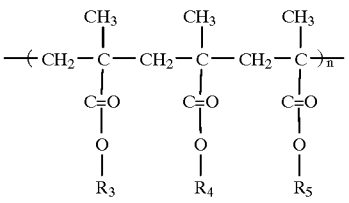

herein $R_3$, $R_4$ and $R_5$ are selected from the same or different polyfluorinated alkyl side chains, $R_3$, $R_4$ and $R_5$ occur in random order, and n is a distribution of integers such that $5<n<1000$.

5. A pressure-sensitive paint composition according to claim 4 utilizing a polymer wherein $R_3$, $R_4$ and $R_5$ are each hexafluorobutyl groups.

6. A pressure-sensitive paint composition according to claim 4 utilizing a polymer wherein $R_3$ is a hexafluoroisopropyl group, $R_4$ is a hexafluorobutyl group, and $R_5$ is selected from either hexafluoroisopropyl or hexafluorobutyl groups.

7. A pressure-sensitive paint composition according to claim 4 utilizing a polymer wherein $R_3$ is a hexafluoroisopropyl group, $R_4$ is a hexafluorobutyl group, and $R_5$ is a dodecafluoroheptyl group.

8. A pressure-sensitive paint composition according to claim 4 utilizing a polymer wherein $R_3$ is a hexafluorobutyl group, $R_4$ is a dodecafluoroheptyl group, and $R_5$ is selected from either hexafluorobutyl or dodecafluoroheptyl groups.

9. A pressure-sensitive paint composition for coating a surface for oxygen pressure sensing applications, said composition consisting essentially of a polymeric binder and an oxygen pressure-sensing dye, wherein said binder consists essentially of a polyfluorinated acrylic polymer having the configuration:

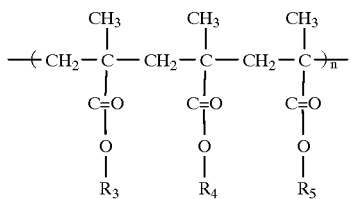

wherein at least one of $R_3$, $R_4$ and $R_5$ is selected from the group consisting of perfluorinated or dihydroperfluorinated alkyl side chains and the remaining two side chains are selected from the same or different perfluorinated or dihydroperfluorinated alkyl side chains or polyfluorinated alkyl side chains, $R_3$, $R_4$ and $R_5$ occur in random order, and n is a distribution of integers such that $5<n<1000$.

10. A pressure-sensitive paint composition according to claim 9 utilizing a polymer wherein $R_3$, $R_4$ and $R_5$ are each dihydroperfluorobutyl groups.

11. A pressure-sensitive paint composition according to claim 9 utilizing a polymer wherein $R_3$ is a dihydroperfluorobutyl group, $R_4$ is a hexafluoroisopropyl group, and $R_5$ is selected from either dihydroperfluorobutyl or hexafluoroisopropyl groups.

12. A pressure-sensitive paint composition according to claim 9 utilizing a polymer wherein $R_3$ is a dihydroperfluoro-n-octyl group, $R_4$ is a dihydroperfluorobutyl group, and $R_5$ is a hexafluoroisopropyl group.

13. A method for measuring the pressure of an oxygen-containing fluid on a surface comprising tie steps of coating a pressure-sensitive paint composition on said surface, exposing said surface to said fluid, and monitoring the resultant quenching of luminescence, wherein said pressure-sensitive paint composition consists essentially of an oxygen pressure-sensing dye dissolved or dispersed in a polymeric binder, said binder being selected from the group consisting of:

A. a fluoroacrylic polymer having the configuration:

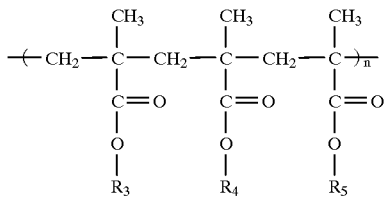

wherein $R_3$, $R_4$ and $R_5$ are selected from the same or different polyfluorinated alkyl side chains, $R_3$, $R_4$ and $R_5$ occur in random order, and n is a distribution of integers such that $5<n<1000$; and, B. a polyfluorinated acrylic polymer having the configuration:

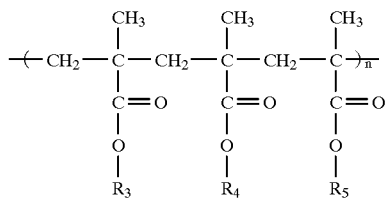

wherein at least one of $R_3$, $R_4$ and $R_5$ is selected from the group consisting of perfluorinated or dihydroperfluorinated alkyl side chains and the remaining two side chains are selected from the same or different perfluorinated or dihydroperfluorinated alkyl side chains or polyfluorinated alkyl side chains, and $R_3$, $R_4$ and $R_5$ occur in random order, and n is a distribution of integers such that $5<n<1000$.

14. A method according to claim 13 wherein said pressure-sensing dye is selected from the group consisting of platinum octaethylporphyrin and platinum tetrapentafluorophenylporphyrin, and said binder is selected from the group consisting of:

poly(2,2,3,4,4,4-hexafluorobutyl methacrylate);

poly(1H,1H-dihydroheptafluorobutylmethacrylate);

poly(1,1,1,3,3,3-hexafluoroisopropylmethacrylate-co-2,2,3,4,4-hexafluorobutyl methacrylate);

poly(1,1,1,3,3,3-hexafluoroisopropyl methacrylate-co-2,2,3,4,4,4-hexafluorobutyl methacrylate-co-1H,1H-7H-dodecafluoroheptyl methacrylate);

poly(2,2,3,4,4,4-hexafluorobutyl methacrylate-co-1H,1H, 7H-dodecafluoroheptyl methacrylate);

poly(1H, 1H-dihydroheptafluorobutylmethacrylate-co-1H,1H-dihydropentafluoropropylmethacrylate);

poly(1H,1H-dihydroheptafluorobutylmethacrylate-co-1H,1H-dihydrotrifluoroethylmethacrylate);

poly(1H,1H-dihydropentafluoropropylmethacrylate-co-1H,1H-dihydrotrifluoroethylmethacrylate);

poly(1H,1H-dihydroheptafluorobutylmethacrylate-co-1,1,1,3,3,3-hexafluoroisopropylmethacrylate);

poly(1H, 1H-dihydroperfluoro-n-octylmethacrylate-co-1H,1H,-dihydroperfluorobutylmethacrylate-co-1,1,1,3,3,3-hexafluoroisopropylmethacrylate);

poly(1,1,1,3,3,3-hexafluoroisopropylmethacrylate-co-2,2,3,4,4,4-hexafluorobutylmethacrylate-co-t(trimethylsiloxy)silylpropylmethacrylate);

poly(1H,1H-dihydroheptafluorobutylmethacrylate-co-tris(trimethylsiloxy)silylpropylmethacrylate); and poly(1,1,1,3,3,3-hexafluoroisopropylmethacrylate-co-1H,1H-dihydroheptafluorobutylmethacrylate-co-tris(trimethylsiloxy)silylpropylmethacrylate).

15. A method for measuring the pressure of an oxygen-containing fluid on a surface comprising the steps of coating a pressure-sensitive paint composition on said surface, exposing said surface to said fluid, and monitoring the resultant quenching of luminescence, wherein said pressure-sensitive paint composition consists essentially of an oxygen pressure-sensing dye dissolved or dispersed in a polymeric binder, wherein said binder consists essentially of a fluoroacrylic polymer having the configuration:

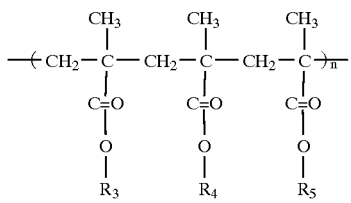

wherein $R_3$, $R_4$ and $R_5$ are selected from the same or different polyfluorinated alkyl side chains, $R_3$, $R_4$ and $R_5$ occur in random order, and n is a distribution of integers such that $5<n<1000$.

16. A method according to claim 15 utilizing a polymer wherein $R_3$, $R_4$ and $R_5$ are each hexafluorobutyl groups.

17. A method according to claim 15 utilizing a polymer wherein $R_3$ is a hexafluoroisopropyl group, $R_4$ is a hexafluorobutyl group, and $R_5$ is selected from either hexafluoroisopropyl or hexafluorobutyl groups.

18. A method according to claim 15 utilizing a polymer wherein $R_3$ is a hexafluoroisopropyl group, $R_4$ is a hexafluorobutyl group, and $R_5$ is a dodecafluoroheptyl group.

19. A method according to claim 15 utilizing a polymer wherein $R_3$ is a hexafluorobutyl group, $R_4$ is a dodecafluoroheptyl group, and $R_5$ is selected from either hexafluorobutyl or dodecafluoroheptyl groups.

20. A method for measuring the pressure of an oxygen-containing fluid on a surface comprising the steps of coating a pressure-sensitive paint composition on said surface, exposing said surface to said fluid, and monitoring the resultant quenching of luminescence, wherein said pressure-sensitive paint composition consists essentially of an oxygen pressure-sensing dye dissolved or dispersed in a polymeric binder, wherein said binder consists essentially of a polyfluorinated acrylic polymer having the configuration:

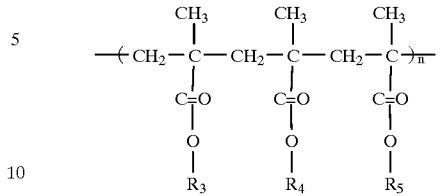

wherein at least one of $R_3$, $R_4$ and $R_5$ is selected from the group consisting of perfluorinated or dihydroperfluorinated alkyl side chains and the remaining two side chains are selected from the same or different perfluorinated or dihydroperfluorinated alkyl side chains or polyfluorinated alkyl side chains, and $R_3$, $R_4$ and $R_5$ occur in random order, and n is a distribution of integers such that $5<n<1000$.

21. A method according to claim 20 utilizing a polymer wherein $R_3$, $R_4$ and $R_5$ are each dihydroperfluorobutyl groups.

22. A method according to claim 20 utilizing a polymer wherein $R_3$ is a dihydroperfluorobutyl group, $R_4$ is a hexafluoroisopropyl group, and $R_5$ is selected from either dihydroperfluorobutyl or hexafluoroisopropyl groups.

23. A method according to claim 20 utilizing a polymer wherein $R_3$ is a dihydroperfluoro-n-octyl group, $R_4$ is a dihydroperfluorobutyl group, and $R_5$ is a hexafluoroisopropyl group.

24. A method according to claim 13 wherein said pressure-sensing dye is selected from the group consisting of platinum octaethylporphyrin and platinum tetrapentafluorophenylporphyrin.

* * * * *

UNITED STATES PATENT AND TRADEMARK OFFICE
CERTIFICATE OF CORRECTION

PATENT NO.    : 5,965,642
DATED         : October 12, 1999
INVENTOR(S)   : Martin P. Gouterman et al.

It is certified that error appears in the above-identified patent and that said Letters Patent is hereby corrected as shown below:

<u>Column 1,</u>
Line 5, after the title, insert paragraph -- This invention was made with government support under Contract Number NCA2-2002 awarded by the National Aeronautics and Space Administration (NASA). The government has certain rights in the invention. --

Signed and Sealed this

Tenth Day of June, 2003

JAMES E. ROGAN
*Director of the United States Patent and Trademark Office*